United States Patent
Hechler et al.

(10) Patent No.: US 7,488,845 B2
(45) Date of Patent: Feb. 10, 2009

(54) METHOD FOR THE SAFE OPERATION OF A GAS-PHASE PARTIAL OXIDATION

(75) Inventors: Claus Hechler, Ludwigshafen (DE); Peter Schlemmer, Eisenberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 57 days.

(21) Appl. No.: 11/555,485

(22) Filed: Nov. 1, 2006

(65) Prior Publication Data

US 2007/0117999 A1    May 24, 2007

Related U.S. Application Data

(60) Provisional application No. 60/738,994, filed on Nov. 23, 2005.

(30) Foreign Application Priority Data

Nov. 23, 2005    (DE) ........................ 10 2005 055 826

(51) Int. Cl.
*C07C 51/16* (2006.01)

(52) U.S. Cl. ....................... 562/545; 562/547; 562/532; 562/512.2; 431/268

(58) Field of Classification Search ................. 562/545, 562/547, 532, 512.2; 431/268
See application file for complete search history.

(56) References Cited

U.S. PATENT DOCUMENTS

| 7,074,955 | B2 | 7/2006 | Hammon et al. |
| 7,102,030 | B2 * | 9/2006 | Sanada et al. ................ 562/545 |
| 7,115,775 | B2 | 10/2006 | Buschulte et al. |
| 2002/0037488 | A1 * | 3/2002 | Hirao et al. ................. 431/268 |
| 2004/0181090 | A1 | 9/2004 | Sanada et al. |

FOREIGN PATENT DOCUMENTS

| DE | 101 17 678 A1 | 10/2002 |
| DE | 102 32 482 A1 | 1/2004 |
| DE | 10 2005 052 923 A1 | 5/2007 |

* cited by examiner

*Primary Examiner*—Daniel M Sullivan
*Assistant Examiner*—Sudhakar Katakam
(74) *Attorney, Agent, or Firm*—Oblon, Spivak, McClelland, Maier & Neustadt, P.C.

(57) ABSTRACT

A method for the safe operation of a continuously operated heterogeneously catalyzed gas-phase partial oxidation of an organic compound in a reactor, the composition of the feed gas mixture being controlled by pressure-controlled concentration determination of relevant constituents.

18 Claims, 1 Drawing Sheet

Figure
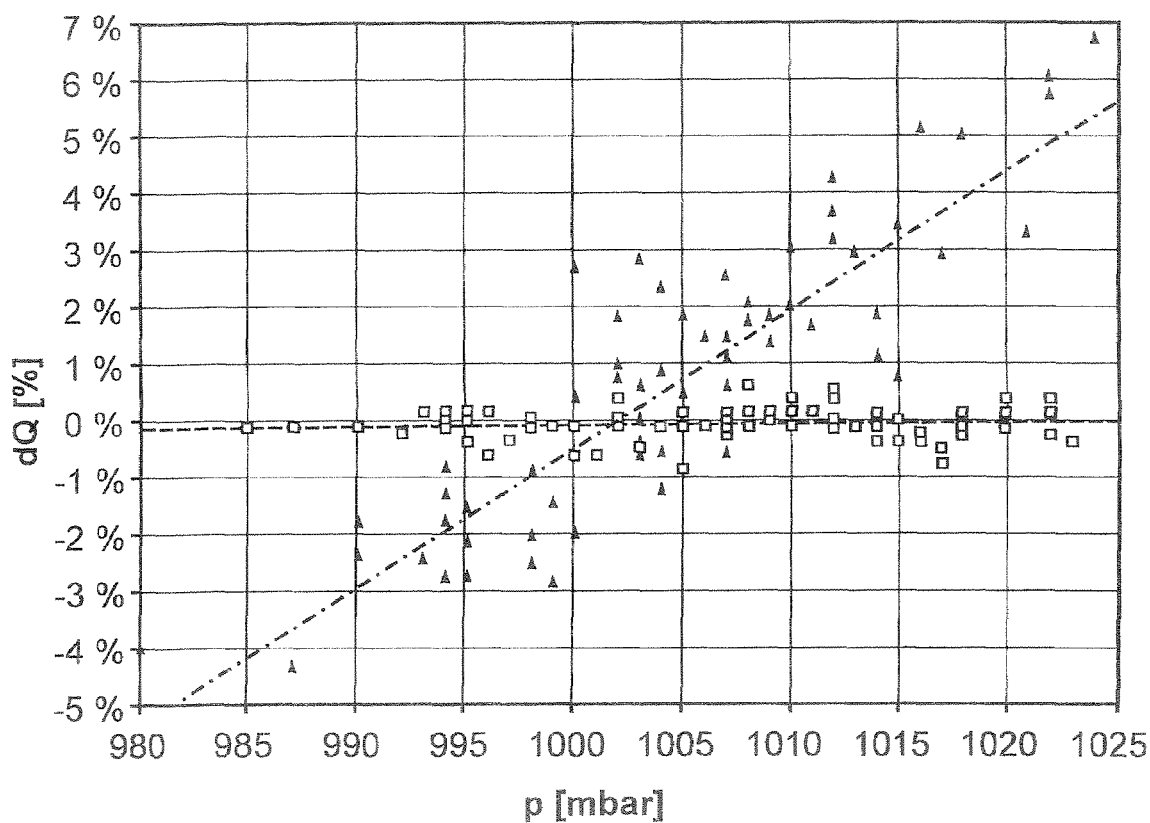

METHOD FOR THE SAFE OPERATION OF A GAS-PHASE PARTIAL OXIDATION

The invention relates to a method for the safe operation of a continuously operated heterogeneously catalyzed gas-phase partial oxidation of at least one organic starting compound in a reactor whose feed gas mixture stream comprises at least one diluent gas substantially inert under the conditions of the heterogeneously catalyzed gas-phase partial oxidation, in addition to the at least one organic starting compound to be partially oxidized and molecular oxygen as an oxidizing agent and is produced by combining at least two different starting streams, in which inclusion of the online measurement of the concentration of one or more selected constituents in the feed gas mixture stream itself, in one or more of the starting streams producing the feed gas mixture stream and/or in the product gas mixture stream prevents the reactor from being fed with an explosive feed gas mixture stream or a feed gas mixture stream which is otherwise uncontrollable, where, for the online measurement, a part-stream of the gas stream to be analyzed in each case is passed continuously (on one side) into a measuring cell of an analytical apparatus and, while the measurement is being carried out, is passed (on another side) out of the measuring cell of the analytical apparatus into a discharge atmosphere.

The partial oxidation of an organic starting compound with molecular oxygen as an oxidizing agent is understood as meaning those reactions of the organic starting compound in the presence of molecular oxygen to give at least one target compound differing from CO, $CO_2$ and $H_2O$, in which reactions the oxidation number of at least one carbon atom in the at least one organic target compound is greater than in the organic starting compound. Partial oxidations are therefore in particular all reactions of an organic starting compound with molecular oxygen to give at least one target compound differing from CO, $CO_2$ and $H_2O$ and comprising at least one oxygen atom more than the organic starting compound. In particular, oxydehydrogenations and oxidative dehydrogenations (in the latter, molecular hydrogen is formed at least as an intermediate and is at least partly oxidized in a subsequent step to $H_2O$) of saturated hydrocarbons to unsaturated hydrocarbons are also partial oxidations (e.g. of propane to propylene).

Partial oxidations of organic starting compounds are widely used for the preparation of organic target compounds (for example, the preparation of acrylic acid from propene and/or propane, the preparation of ethylene oxide from ethylene, the preparation of methacrylic acid from isobutene and/or isobutane or the preparation of propylene from propane). For this purpose, usually at least two material starting streams, namely at least one starting stream comprising the at least one organic starting compound (the starting substance or substances of the reaction) and at least one starting stream comprising molecular oxygen, are mixed with one another to give the feed gas mixture stream, the mixture being capable, with suitable activation (for example by means of a catalyst), of reacting in an undesired manner to give a product gas mixture stream comprising the at least one target compound. The starting substances of the chemical reaction (organic starting compounds) which are to be used here, however, predominantly have the property, in the presence of molecular oxygen, of being able to undergo not only the desired reaction to give the target compound but also to undergo undesired reactions in certain composition ranges of the feed gas mixture, this course of the reaction as a rule not being deliberately triggered (i.e. usually being present unintentionally) (e.g. an undesired ignition source, such as a spark or an unintentionally overheated surface) and then being able to develop with very considerable pressure increase in a deflagrative manner as an explosion or even as a detonation.

Safe control of the effects of all possible undesired courses of reaction would be possible, if at all only at an enormous cost, for example by an exceedingly expensive design of the reaction apparatuses, which then have to be dimensioned for much higher pressure than can occur in normal operation, and it is for this reason that there is a major economic potential in the reliable avoidance of certain dangerously explosive feed gas mixture compositions from the outset for preventing certain undesired courses of reaction. Since the reactants are consumed in the course of a partial oxidation, the reaction gas mixtures arising in the course of a partial oxidation from the feed gas mixture are as a rule readily controllable whenever the feed gas mixture itself is readily controllable.

The guideline to Directive 1999/92/EC of the EU Commission in the final version of April 2003 gives a basic synopsis as well as a procedure and conservation appropriate to the prior art and the rules.

General avoidance of ignitable feed gas mixtures is achievable if the content of the organic fractions in the feed gas mixture is kept safely below the minimum value required for ignitability (lower explosion limit; by the concomitant use of inert diluent gases (i.e. gases which remain unchanged to an extent of at least 95 mol %, preferably to an extent of at least 98 mol % or more, in the course of the partial oxidation; typical inert diluent gases are, for example, molecular nitrogen, noble gases and steam; however, inert diluent gas may also be a spontaneously ignitable gas, such as, for example, propane in the case of a partial oxidation of propylene to propylene oxide), the course of explosion limits can be influenced). With the use of measuring apparatuses according to the prior art which control the abovementioned content, such a procedure results as a rule in feed gas mixtures having such a low concentration (lying very much below the possible limiting concentration) that the desired reaction is economically disadvantageous or inexpedient.

An alternative possibility for avoiding ignitable feed gas mixtures is the safe increase of the concentration of the organic fractions beyond a maximum value, the so-called upper explosion limit. The disadvantage of such a procedure is that, with the use of measuring apparatuses according to the prior art which control this concentration, the resulting feed gas mixtures have as a rule, with regard to the target reaction, compositions (lying very far above this upper limit) which firstly are not very reactive, so that only low reaction rates result and secondly generally have a very large excess of organic starting substance of the reaction, giving rise to the necessity of separating this excess from the resulting product gas mixture and recycling it into the feed gas mixture, both of which are economically disadvantageous. Furthermore, an excess of the concentration of the organic fractions relative to the reaction stoichiometry usually has an adverse effect on the catalyst life.

A third possibility is, for example to reduce the concentration of molecular oxygen in the feed gas mixture below a lower limiting value, so-called limiting oxygen concentration. Regardless of the other composition of the feed gas mixture, ignitions are then no longer possible. With the use of measuring apparatuses according to the prior art which control the oxygen concentration, this requires a concentration significantly below the abovementioned limiting concentration, as a result of which, as a rule, it is likewise not possible to achieve high reaction and conversion rates.

In order to avoid these disadvantages, there is a need for measuring apparatuses which control the contents or concentrations and, in regular operation, also ensure as substantial utilization as possible of the still safe composition range in the sense of approaching the limits of ignitable feed gas mixture composition as substantially as possible but still safely, and which, through the resulting high partial pressures of the reactants permit the maximum possible conversion densities and conversion rates particularly for the desired course of reaction of the partial oxidation and hence as a rule the economically most advantageous mode of operation.

In various heterogeneously catalyzed partial gas-phase oxidations (for example in the partial oxidation of xylenes to phthalic anhydride), it is, with regard to the course of the reaction and an economically expedient mode of operation even desirable to establish feed gas mixture compositions which are within the range of ignitable compositions but whose behavior in the case of an undesired ignition is safely controllable at a cost which is still comparatively limited by suitable equipping and/or design of the plant. However, complete exhaustion of the abovementioned option requires measuring apparatuses which control contents/concentrations and ensure that the ignition limits are exceeded to a safely limited extent, i.e. in an exactly controlled manner, and rule out penetration into ignitable feed gas regimes to an impermissible depth with possibly no longer controllable courses of the reaction.

The possibility of being able to carry out certain partial oxidative preparation processes in an economically expedient manner is often realized at all only by limiting in a controlled manner the exceeding of the limits of the ignition region assignable to the organic constituents of a feed gas mixture and the simultaneous maintenance of a sufficiently safe difference between the feed gas mixture composition and, for example, ignitable stoichiometric mixtures, i.e. those mixtures in which the molar ratios of reactive oxygen and organic constituents are stoichiometrically ideal for complete combustion of the carbon of the organic constituents to $CO_2$, and in which as a result the effects of undesired ignitions in the form of, for example, drastic pressure and temperature increase would be the strongest, i.e. most disadvantageous and the least controllable.

It is therefore of considerable interest and advantage, by suitable control and limiting measures, safely to permit the limits of ignitable feed gas compositions either to be approached as far as possible without these limits being exceeded or to exceed these limits just so far that the effects of an unplanned reaction in the case of exceeding in such a manner are still controllable in terms of the apparatus in an economically advantageous manner. The basis of such control and limiting measures is as exact knowledge as possible of the various process parameters and here in particular of the concentrations of the relevant constituents of the feed gas mixture which are present, as mentioned, for example, in the publication DE-A 102 32 482. in order to obtain this knowledge, it is customary for the concentrations of selected constituents in the feed gas mixture stream itself, in one or more of the starting streams for producing the feed gas mixture stream and/or in the product gas mixture stream produced by the gas-phase partial oxidation (for example of residue molecular oxygen still present in the product gas mixture stream and unconverted in the partial oxidation) to be determined experimentally online, the results obtained to be fed back to the production of the feed gas mixture stream and, in the extreme case the partial oxidation to be stopped by withholding organic starting substance (cf. DE-A 102 32 482).

A feed gas mixture which is no longer controllable may, however, also be present when the content of molecular oxygen in the feed gas mixture is too low so that the catalysts which as a rule comprise multielement oxide materials and are usually extremely expensive to prepare are no longer sufficiently reoxidized during the partial oxidation and may therefore be irreversibly damaged, which in the end also entails stoppage of the partial oxidation. Otherwise, after the target product has been separated from the product gas mixture stream, the latter may also itself be starting stream for the production of the feed gas mixture stream in a partial or complete recycle gas procedure.

US-A 2004/0181090 states that the measuring apparatuses or systems of the prior art for determining such gas concentrations have considerable inaccuracy and are therefore not sufficiently trustworthy. As an alternative to increased safety margins from the permissible limiting compositions, it is proposed, as a possible solution, to assume the presence of an error only on simultaneous indication of the impermissible state by a second comparative or control method and to bring about a shutdown of the gas-phase partial oxidation However, this is not very satisfactory and leads to virtually twice as high an installation effort with correspondingly uneconomical costs, questionable reliability having to be accepted at least for some of the apparatuses.

Our own investigations of the possible causes of abovementioned inaccuracies have produced the following.

The predominant number of known measuring methods for the online determination of concentrations in gas mixture determine a particle density (number of particles per unit volume) of the species to be determined in a predetermined gas volume (e.g. the volume of a measuring cell). The number of particles, e.g. molecules, in the measured volume obeys the recognized physical laws in the area of phenomenological thermodynamics and, in the range of validity of the ideal gas law which can typically be assumed for such measures is directly proportional to the absolute pressure and inversely proportional to the absolute temperature in the measured volume.

For example, the concentration determination (in particular in the case of molecular oxygen) can be effected by the procedures described in the publications DE-A 10117678 and DE-A 102005052923. The basis of these is, inter alia, that electromagnetic radiation having a wavelength at which the species to be determined absorbs is passed through the measuring cell of the analytical apparatus and that fraction of the electromagnetic radiation which is not absorbed by the species to be determined which is present in the measuring cell is measured behind the measuring cell.

For example, the oxygen concentration can be measured by means of a laser beam whose wavelength is adjusted to one of the rotational fine structure bands of molecular oxygen. For calibrating the measurement, the laser beam can pass through a calibration cell which comprises a gas having a defined oxygen content or through which a gas having a defined oxygen content is passed. For example, the abovementioned laser may be a diode laser whose wavelength can be adjusted to one of the rotational fine structure bands of molecular oxygen in the range of from 759.5 to 768 nm. The modulation range may be +0.05 nm. In principle, for example a gas analysis apparatus of the Ultramat® 23 type from Siemens can be used for the purpose according to the invention (operates in the IR range). The abovementioned measuring method is suitable in particular for the simultaneous determination of propane and/or propylene in the infrared range (IR). Inter alia measuring apparatuses of the type MCS 100 (multifrequency apparatus) or of the type Unor®, in each case from Sick-Maihak in Reute, Germany may be suitable for this purpose.

However, measuring methods which are based on completely different relationships are also suitable for the method according to the invention. For example, molecular oxygen has a comparatively high paramagnetic susceptibility This is utilized by oxygen analyzers of the Oxymat® series from Siemens and by oxygen analyzers of PMA® series from M&C Products Analysentechnik GmbH in D-40885 Ratingen, Germany. These are analytical apparatuses which, owing to their very rapid response time, their small dead volume, their low cross-sensitivity to other gas constituents and to the direct flowability through the measuring cell, are particularly advantageous (e.g. the version PMA 30). The measuring methods based on the abovementioned principle are among the most accurate quantitative methods of determination for molecular oxygen in the range from 0 to 100% by volume. A diamagnetic handle having a mirror present at the pivot point is fastened to tensioning belts in the abovementioned apparatuses and mounted in an inhomogeneous magnetic field. Owing to its paramagnetism the oxygen strives to enter the inhomogeneous magnetic field of the measuring cell. The $O_2$ molecules exert a torque on the handle and cause it to deflect according to the oxygen concentration. Optical scanning electronically generates a current which flows through a wire loop which is placed around the handle and turns the latter back to the neutral position. The compensation current is proportional to the oxygen content of the measuring gas, with the result that the $O_2$ indication is absolutely linear.

In principle, however, gas chromatographic or electrochemical methods are also suitable. In the latter, the species to be analyzed is ionized by suitable energy supply, and the electrical conductivity of the gas present in the measuring cell is continuously determined.

According to the methods of the prior art for the purpose of carrying out an online analysis of a gas stream, a part-stream of the same composition is usually taken from this gas stream by means of a suitable quantitative metering apparatus and then flows, either on the basis of the gradient between the pressure in the gas stream to be analyzed and the pressure in the measured volume (in the measuring cell of the measuring apparatus) and/or by a transport apparatus which generates such a pressure gradient, into the measured volume (into the measuring cell) of the measuring apparatus and from there, once again on the basis of the pressure gradient, to a discharge atmosphere (i.e. the atmosphere into which the part-stream is let down after the measurement has been carried out); most simply, this may be the ambient atmosphere; the discharge atmosphere can, however, also be an artificially produced atmosphere, for example the atmosphere of a space present under reduced pressure by means of a vacuum pump (or under superatmospheric pressure), as a rule virtually the same pressure as that of the discharge atmosphere but in particular the variations of the discharge atmosphere being established within the measured volume (within the measuring cell) owing to the very small pressure drop in the discharge line.

In a corresponding manner, pressure variations also form in the gas stream to be analyzed in the measuring cell.

However, changes and/or variations of pressure and/or temperature in the measured volume (the measuring cell) lead directly to changes to values of the concentration to be determined and are presumably the cause of the problems discussed in US-A 2004/0181090. In addition, owing to the necessity of maintaining safely determined minimum differences from the above-described ignitable compositions to be avoided, they require a limitation of the accessible concentration range for the desired partial oxidation, since the inaccuracies discussed must be taken into account by an increased safety margin. Alternatively, a control variant according to the teaching of US-A 2004/0181090 is required.

It was therefore an object of the present invention to permit the concentration measurement of especially those substances of a feed gas mixture for a partial oxidation which are relevant with regard to the safety in respect of ignition basically with such a high accuracy that this measurement is not the limiting element with regard to the safely useable composition range of the feed gas, and at the same time it is possible to dispense with an expensive method limited with regard to the feasibility in terms of safety, as described in US 2004/0181090.

The achievement consists in a method for the safe operation of a continuously operated heterogeneously catalyzed gas-phase partial oxidation of at least one organic starting compound in a reactor whose feed gas mixture stream comprises at least one diluent gas substantially inert under the conditions of the heterogeneously catalyzed gas-phase partial oxidation, in addition to the at least one organic starting compound to be partially oxidized and molecular oxygen as an oxidizing agent and is produced by combining at least two different starting streams, in which inclusion of the online measurement of the concentration of one or more selected constituents in the feed gas mixture stream itself, in one or more of the starting streams producing the feed gas mixture stream and/or in the product gas mixture stream prevents the reactor from being fed with an explosive feed gas mixture stream or a feed gas mixture stream which is otherwise controllable, where, for the online measurement, a part-stream of the gas stream to be analyzed in each case is passed continuously into a measuring cell of an analytical apparatus and, while the measurement is being carried out, is passed (discharged) out of the measuring cell of the analytical apparatus into an atmosphere (the "discharge atmosphere"), the gas stream to be analyzed, and/or the discharge atmosphere, being subject to pressure variations, wherein the influence of variations of the pressure of the gas stream to be analyzed and/or of the discharge atmosphere on the measured pressure in the measuring cell in the analytical apparatus and hence on the result of the measurement a) is computationally correct and/or b) minimized by keeping constant or regulated the measured pressure in the measuring cell of the analytical apparatus independently of the pressure of the gas stream to be analyzed and/or of the discharge atmosphere by means of a pressure control apparatus.

By far the most measuring methods for the online determination of concentrations in the gas phase determine, as mentioned above, the particle density of the substance to be analyzed. The number of particles, e.g. molecules, per measured volume obeys the recognized physical laws and, within the scope of validity of the ideal gas law, is directly proportional to the absolute pressure in the measured volume and inversely proportional to the absolute temperature in the measured volume. With a knowledge of pressure and temperature in the measuring cell, the abovementioned computational correction is therefore possible in a comparatively simple manner.

It was furthermore found that the substantial external influencing factor (not associated with the actual principle of measurement) of such a measurement by methods according to the prior art is in particular the variation of the measured pressure in the measuring cell, which can be reduced by pressure control measures to a substantially vanishing degree, with the result that the switching off of the operated gas-phase partial oxidation previously brought about prematurely owing to safety-based tolerances can be substantially avoided or takes place more rarely and/or later on, with the consequence of better cost-efficiency by very substantial utilization of the feed gas composition ranges permissible with regard to safety and by better or more intensive reaction owing to the higher reactivity of the feed gas mixture.

As described above, according to the methods of the prior art for the purpose of carrying out an online analysis of a gas stream, a part-stream of the same composition is taken from this gas stream, usually by means of a suitable quantitative metering apparatus (in the simplest case a fixed or a variable cross section) and then flows, either on the basis of the gradient between the pressure in the gas stream to be analyzed and the pressure in the measured volume (in the measuring cell of the measuring apparatus) and/or by a transport apparatus which generates such a pressure gradient into the measured volume (into the measuring cell) of the measuring apparatus and from there, once again on the basis of the pressure gradient, to a discharge atmosphere (i.e. the atmosphere into which the part-stream is discharged or passed after the measurement has been carried out; or simply, this may be the ambient atmosphere; the discharge atmosphere can, however, also be an artificially generated atmosphere, for example the atmosphere of a space present under reduced pressure by means of vacuum pumps) into said discharge atmosphere.

A pressure of the discharge atmosphere which has been imposed on the measuring apparatus in the measured volume (in the measuring cell) by this procedure according to the prior art can, according to the present invention, now be decoupled from the pressure of the discharge atmosphere and regulated in a simple manner by the intermediate connection (between measuring cell and discharge atmosphere) of an adjustable and/or controllable flow-through orifice. Depending on the pressure states in the measured volume (in the measuring cell) and in the discharge atmosphere, this flow-through orifice is varied in such a way that a substantially constant pressure prevails in the measured volume (in the measuring cell), independently of the pressure in the discharge atmosphere and also independently of the part-stream flowing into the measured volume (into the measuring cell).

This means that the basic principle of the pressure control according to the invention comprises regulating the part-stream flowing through the measuring cell of the analytical apparatus to a value independent of the respective actual pressures in the discharge atmosphere or in the gas stream to be analyzed.

According to the invention, this basic principle is expediently carried out by means of a pressure control apparatus arranged between measuring cell and discharge atmosphere and in the form of an adjustable passage, for example in the development of a control valve having a suitable adjusting drive apparatus (for example a movable needle with conical cross section). Suitable drive energies are both energies of the measuring system itself, such as, for example, pressure differences acting on membranes (for example the pressure difference existing between discharge atmosphere and measuring cell or the pressure difference existing between measuring cell and gas stream to be analyzed) and external energies, such as, for example, gas and liquid pressures decoupled from the actual measuring system (for example "compressed air") and/or mechanical energy applied, for example, by means of spring(s).

A controlled equilibrium between the amount of gas flowing from the gas stream to be analyzed from the gas-phase partial oxidation into the measured volume (into the measuring cell) and the amount of gas flowing out of the measured volume into the discharge atmosphere is thus established, with the effect of maintaining a virtually constant pressure in the measured volume itself.

The introduction of a further appropriately designed pressure control apparatus between gas stream to be analyzed and measuring cell additionally improves the pressure constancy in the measuring cell.

According to the invention, in addition to the use of a pressure control according to the invention, it is expedient to reduce the influence of the variations of the measuring temperature on the result of the measurement by keeping the temperature of the measured volume (of the measuring cell) constant by regulation. For this purpose, the analytical apparatus or the analytical apparatuses can be placed, for example, in a conditioned room. Thermostating of the measuring cell within the analytical apparatus is, however, frequently sufficient.

The method according to the invention is provided for the online measurement of the concentration of one or more selected constituents in the feed gas mixture stream itself, in the product gas mixture stream and/or in one or more of the starting streams producing the feed gas mixture stream, i.e. for concentration measurement during ongoing operation of a continuous heterogeneously catalyzed gas-phase partial oxidation.

The pressure control apparatus to be used according to the invention for keeping the measured pressure in the measuring cell of the analytical apparatus constant independently of the actual pressure of the discharge atmosphere or regulating said measured pressure can advantageously be in the form of an integral, compact unit which in particular may be commercially available, and as such is expediently installed at the outlet of the gas stream from the measuring cell, i.e. between the analytical apparatus and the discharge atmosphere.

It is also possible for the pressure control apparatus to be in the form of a noncompact unit, two or more of the functional units constituting it—measuring apparatus, control apparatus and actuator (flow controller including drive)—to be in the form of units separated mechanically from one another. Thus, a measuring apparatus determines the actual pressure in the measured volume (in the measuring cell) and then sends a signal to the control apparatus, which in turn sends an adjusting signal to an actuator, which varies the flow-through cross section and thus adjusts the pressure in the measured volume.

A transport apparatus for the part-stream or part-streams to be analyzed, whose concentration of one or more selected constituents is measured can advantageously be introduced in addition to the pressure control apparatus at the outlet of the gas from said apparatus, i.e. between pressure control apparatus and discharge atmosphere.

The transport apparatus can advantageously be a diaphragm pump, but in general other generally customary pumps, e.g. piston metering pumps or peristaltic pumps, or other specially adapted pumps can also be used. Single-stage pumps, in particular gas diaphragm pumps, especially of the type M56ex from KNF-Neuberger D-Freiburg i. Br., Germany, have proven useful, and, for example, gas diaphragm pumps of the type N86 and N87 from KNF-Neuberger D-Freiburg i. Br., Germany and bellows pumps of the series P 2.2 to P 2.6 or US-P 2.6 from Bühler D-Ratingen, Germany are also suitable. Diaphragm pumps, for example of the type FM 1101 from Fürgut in D-Tannheim, Germany are also suitable.

In this embodiment comprising a transport apparatus, it is possible to work with a stable measured pressure in the measuring cell of the analytical apparatus or of the analytical apparatuses, which measured pressure differs in a substantially arbitrary manner from the pressure in the discharge atmosphere. In one embodiment, the measured pressure may be below the pressure of the discharge atmosphere; in another embodiment, however, it may also be equal to or higher than the pressure of the discharge atmosphere.

With regard to the accuracy of measurement, it is advantageous to work at an excess pressure relative to the pressure in the discharge atmosphere, because as a result, even in the case of very small leaks due to manufacture, no gases penetrate from outside into the measured volume (into the measuring cell), which gases might falsify the result of the measurement. This variant of the method is expedient, for example, particularly when the constituent of the gas stream which is to be analyzed and the concentration of which is measured is oxygen, since the atmosphere surrounding the measuring apparatus and hence the measured volume is as a rule oxygen-containing air.

If, on the other hand, the gas stream which is to be analyzed and of which the concentration of at least one constituent is measured comprises a toxic substance, a measurement at reduced pressure is frequently preferable to a measurement at the pressure in the discharge atmosphere (frequently the natural measuring environment), in order to avoid leaks of the toxic substance to the outside. However, the greater safety is in certain circumstances achieved at the cost of a limited accuracy of measurement owing to the penetration of external gas.

Particularly expediently according to the invention, the pressure inside the measuring cell will differ by not more than +100 mbar from the pressure in the discharge atmosphere or from the pressure in the gas stream to be analyzed. This situation arises because the pressure control loop according to the invention must react generally very sensitively in order to achieve a high accuracy of measurement. As a rule, large pressure differences have an adverse effect on such a required pressure sensitivity.

In a further advantageous development of the procedure according to the invention, part-streams of two or more gas streams which are independent of one another and to be analyzed independently of one another can be fed in each case to an appropriate number of analytical apparatuses operated in parallel for the measurement of the respective concentration of one or more of their constituents and, for the purpose of the pressure control of the measurement in each individual analytical apparatus, the gas streams emerging from the analytical apparatuses can be mixed with one another to give one mixture stream and fed only to a single pressure control apparatus and then discharged into the discharge atmosphere. The above variant proves to be advantageous particularly when the different gas stream constituents are chemically compatible with one another.

A substantial advantage of this variant of the method is that the error consideration is identical for all gas streams to be analyzed since the concentrations of one or more selected constituents from all gas streams to be analyzed is determined under identical conditions in each case. Moreover, because only a single pressure control apparatus is required for all measurements, there is also a cost advantage.

The transport apparatus described above for the part-stream or part-streams of the gas streams to be analyzed the concentration of one or more selected constituents of which gas streams is determined, can advantageously be used according to the invention for recycling the part-stream or part-streams to be analyzed into the respective gas stream from which they were taken.

This embodiment with recycling of the analyzed part-streams by means of the transport apparatus into the gas streams of the continuously operated heterogeneously catalyzed gas-phase partial oxidation which are to be analyzed is particularly advantageous particularly in the case of undesired losses of yield or when it is necessary to dispose of special problematic ingredients since appropriate measures in this context are usually already present for other reasons for said disposal in the process (partial oxidation and subsequent isolation of target product).

In a further embodiment, an additional reduction of the deviations of the pressure control apparatus can be achieved by, for example, feeding in a constant additional gas stream (carrier gas stream) after (generally between) the measuring cell or measuring cells and the pressure control apparatus, so that the pressure control apparatus always has a stable minimum flow available. A gas stream which proves to be inert to the partial oxidation (e.g. molecular nitrogen) is advantageously used according to the invention as such a constant additional stream.

Frequently, the selected constituent or one of the selected constituents of the gas stream whose concentration is measured in the analytical apparatus is molecular oxygen.

Frequently, the selected constituent or one of the selected constituents of the gas stream whose concentration is measured in the analytical apparatus may be propylene and/or propane.

Finally, it should be mentioned that the method according to the invention can be used in particular for determining the oxygen content for the process described in DE-A 102005052923. It is furthermore suitable for concentration determinations for the process described in DE-A 102 32 482.

On the basis of the abovementioned, the method according to the invention is particularly suitable for use in a heterogeneously catalyzed partial oxidation of propylene and/or propan to acrolein and/or acrylic acid.

BRIEF DESCRIPTION OF THE DRAWING

The invention is explained in more detail below with reference to a FIGURE and working examples The single FIGURE shows the results of measured value variations of the oxygen concentration measurement in the case of an air pressure change in an analytical apparatus according to the prior art, i.e. without pressure control apparatus for comparison and in an analytical apparatus having a pressure control apparatus according to the invention.

In the single FIGURE, the ambient air pressure (discharge atmosphere is the natural external environment in the measuring space) p in mbar is plotted along the abscissa and the resulting deviation in the respective measurement in the concentration dQ in percent from the actually set concentration value of a reference gas having a certified composition is plotted along the ordinate. The deviations in the measurements are shown for a method according to the prior art, i.e. without pressure control apparatus according to the invention in the measuring cell of the analytical apparatus, by solid triangles. The computationally determined dimensionless deviations of the determined $O_2$ concentration values dQ in % from the actually set, precisely known value of the $O_2$ concentration of a previously prepared test gas are plotted here against the ambient air pressure prevailing in each case, for a large number of measurements carried out on different days. This is also shown for a method according to the invention, comprising pressure control apparatus of the analytical apparatus, by open squares. The species to be determined is molecular oxygen, and the analytical apparatus for the oxygen concentration is an apparatus of the type Siemens Oxymat 5F (from 0 to 10% by volume).

As is evident from the FIGURE, the deviation in the measurement in the method according to the prior art was about ±5%, compared with only about ±0.3% in the method according to the invention. On consideration over an even longer period there would be considerably larger deviations owing to the then even greater air pressure variations due to changing weather conditions.

WORKING EXAMPLES

Comparative Example

A part-stream having the same composition as a gas stream to be analyzed for its residual oxygen content (about 3% by volume) was taken from the product gas stream from a continuously operated reactor for the partial oxidation of propylene to acrylic acid and was fed to a Siemens Oxymat 5F oxygen analysis apparatus which was installed in an unconditioned analytical apparatus room. Consequently, the measuring cell in the analytical apparatus was exposed to variations of about +3° C. in the room temperature in the course of a year, which corresponds to a deviation in the measurement of the $O_2$ content of about ±1% (based on the content) corresponding to the influence of the temperature on the density of the gas to be analyzed.

The part-gas stream to be analyzed was let down from the analytical apparatus into the ambient atmosphere. Variations of the ambient pressure of ±15 mbar led to deviations in the measurements of the $O_2$ content of about +1.5%.

Example 1

The comparative example was repeated, but a pressure controller in the form of a compact unit was introduced downstream of the analytical apparatus, via which pressure controller the part-gas stream to be analyzed was released to the ambient atmosphere. The pressure in the measuring cell of the analytical apparatus was controlled with a tolerance of ±2 mbar. As a result of the pressure control the deviation in the measurement of the $O_2$ content was reduced to about ⅛ compared with the prior art.

By additionally installing the analytical apparatus in a conditioned room and thus keeping the room temperature constant with a tolerance of ±0.5° C., the measuring error due to the temperature influence was additionally reduced to about ⅙ compared with the prior art.

Altogether, it was possible to reduce the deviation of the measurement to below 0.5%, based on the $O_2$ content.

Example 2

Example 1 was repeated, but the pressure control apparatus is in the form of a non-compact unit. Here, a pressure transducer of the type Labom CD1020 from Labom in DE-Hude, Germany as a measuring apparatus determines the actual pressure in the measured volume and then sends a signal via an input card SM331 to a PID controller (has a proportional, an integrating and a differential active component) which is programmed in a Siemens PCS7 process control system and which in turn sends an adjusting signal via an output card SM332 to an actuator (a pneumatically driven Whitey SS45-SB-MM fitting from Swagelok in Solon, Ohio, USA) which varies the flow cross section and thus adjusts the pressure in the measured volume with the result that the deviation in the measurement can be reduced below 0.3% of the $O_2$ content.

Example 3

Example 2 is repeated using a further improved experimental arrangement in which a constant additional $N_2$ stream is fed in behind the analytical apparatus and before the pressure control apparatus. As a result, a further reduction in the deviation of the pressure control apparatus is achieved, so that the deviation of the measurement is only 0.2% of the $O_2$ content.

We claim:

1. A method for the safe operation of a continuously operated heterogeneously catalyzed gas-phase partial oxidation of at least one organic starting compound in a reactor whose feed gas mixture stream comprises at least one diluent gas substantially inert under the conditions of the heterogeneously catalyzed gas-phase partial oxidation, in addition to the at least one organic starting compound to be partially oxidized and molecular oxygen as an oxidizing agent and is produced by combining at least two different starting streams, in which inclusion of an online measurement of the concentration of one or more selected constituents in the feed gas mixture stream itself, in one or more of the starting streams producing the feed gas mixture stream and/or in the product gas mixture stream prevents the reactor from being fed with an explosive feed gas mixture stream or a feed gas mixture stream which is otherwise uncontrollable, where, for the online measurement, a part-stream of the gas stream to be analyzed in each case is passed continuously into a measuring cell of an analytical apparatus providing a measurement of concentration of said one or more selected constituents and, while the measurement is being carried out, is passed out of the measuring cell of the analytical apparatus into a discharge atmosphere, the gas stream to be analyzed, and/or the discharge atmosphere, being subject to pressure variations, wherein in said method the influence of variations of the pressure of the gas stream to be analyzed and/or of the discharge atmosphere on the measured pressure in the measuring cell in the analytical apparatus and hence on the result of the measurement a) is computationally corrected and/or b) minimized by keeping constant or regulated the measured pressure in the measuring cell of the analytical apparatus independently of the pressure of the gas stream to be analyzed and/or of the discharge atmosphere by means of a pressure control apparatus.

2. The method according to claim 1, wherein the pressure control apparatus is in the form of an integral compact unit.

3. The method according to claim 1, wherein the pressure control apparatus is in the form of a non-compact unit.

4. The method according to claim 1, wherein the passage of the part-stream into the measuring cell and/or the discharge of the part-stream from the measuring cell is carried out with the aid of a transport apparatus.

5. The method according to claim 4, wherein the transport apparatus is arranged between pressure control apparatus and discharge atmosphere.

6. The method according to claim 5, wherein the transport apparatus is a diaphragm pump.

7. The method according to claim 1, wherein the pressure in the measuring cell is below the pressure in the discharge atmosphere.

8. The method according to claim 1, wherein the pressure in the measuring cell is higher than the pressure in the discharge atmosphere.

9. The method according to claim 1, wherein the pressure in the measuring cell corresponds to the pressure in the discharge atmosphere.

10. The method according to claim 1, wherein the deviation of the pressure in the measuring cell both from the pressure in the discharge atmosphere and from the pressure in the gas stream to be analyzed is not more than 100 mbar.

11. The method according to claim 1, wherein, after it has been discharged from the measuring cell, the part-stream of the gas stream to be analyzed is recycled into the gas stream to be analyzed.

12. The method according to claim 1, wherein a constant additional stream is fed in between measuring cell and pressure control apparatus.

13. The method according to claim 1, wherein at least one of the selected constituents of the gas stream to be analyzed is molecular oxygen.

14. The method according to claim 1, wherein at least one of the selected constituents of the gas stream to be analyzed is propylene and/or propane.

15. The method according to claim 1, wherein it is carried out in a plurality of analytical apparatuses operated in parallel, and the pressure control for all measuring cells of the various analytical apparatuses is carried out with only one common pressure control, into which the part-streams to be analyzed from the various measuring cells of the various analytical apparatuses are fed as a mixture.

16. The method according to claim 1, wherein the discharge atmosphere is the natural ambient atmosphere.

17. The method according to claim 1, wherein the discharge atmosphere is not the natural ambient atmosphere.

18. The method according to claim 1, wherein the temperature of the measuring cells is additionally kept constant.

* * * * *